United States Patent [19]

Bellani

[11] Patent Number: 5,777,170
[45] Date of Patent: Jul. 7, 1998

[54] PROCESS FOR THE PREPARATION OF A NAPHTHYLBUTANONE

[75] Inventor: Piero Bellani, Rho, Italy

[73] Assignee: Archimica SpA, Italy

[21] Appl. No.: 900,224

[22] Filed: Jul. 24, 1997

[30] Foreign Application Priority Data

Jul. 29, 1996 [IT] Italy .................. MI96A1605

[51] Int. Cl.[6] .................................. C07C 45/59
[52] U.S. Cl. ............................. 568/322; 549/453
[58] Field of Search .................. 568/322; 549/453

[56] References Cited

U.S. PATENT DOCUMENTS

| | | | |
|---|---|---|---|
| 4,180,585 | 12/1979 | Goudie | 424/311 |
| 4,194,010 | 3/1980 | Goudie | 424/341 |
| 4,243,682 | 1/1981 | Goudie et al. | 549/453 |
| 4,303,674 | 12/1981 | Goudie | 549/453 |
| 5,225,603 | 7/1993 | Aslam et al. | 568/315 |
| 5,600,009 | 2/1997 | Fritch et al. | 568/318 |

FOREIGN PATENT DOCUMENTS

| | | |
|---|---|---|
| 0376516 | 7/1990 | European Pat. Off. |
| 2329263 | 5/1977 | France . |
| 670632 | 6/1989 | Switzerland . |

*Primary Examiner*—James H. Reamer
*Attorney, Agent, or Firm*—Michael N. Meller

[57] ABSTRACT

An expedient synthesis of 4-(6-methoxynaphth-2-yl)-2-butanone is carried out by reacting 2-bromo-6-methoxynaphthalene with 3-ethylenedioxybutene in the presence of PdCl$_2$ and triphenylphosphine, hydrogenating the 6-methoxy-2-(3-ethylene-dioxybuten-1-yl)naphthalene obtained and then hydrolysing the latter with an acid.

10 Claims, No Drawings

PROCESS FOR THE PREPARATION OF A NAPHTHYLBUTANONE

The present invention relates to a process for the preparation of 4-(6- methoxynaphth-2-yl)-2-butanone.

4-(6-methoxynaphth-2-yl)-2-butanone is a known drug having antiinflammatory action which is known under its Internation Non-proprietary Name "nabumetone" and is represented by formula A.

Numerous syntheses of this product have been proposed; among these syntheses, the one that gives better yields provides for the reaction of 6-methoxy-2-bromonaphthalene (I) and methyl vinyl ketone in the presence of a catalyst, preferably a bivalent palladium salt, and triphenylphosphine, and for the hydrogenation of the product so obtained (U.S. Pat. No. 5,225,603). According to that method, the reaction with methyl vinyl ketone takes place with optimum yields, provided that it is carried out under high pressure and under an inert atmosphere.

According to a further method (EP 376 516), the 6-methoxy-2-bromonaphthalene is reacted with buten-3-ol in the presence of palladium-based catalysts. In that case, the reaction can take place at ambient temperature, but the yields drop to 65% and the nabumetone obtained has a purity of 76%.

It has now been found that, by reacting 6-methoxy-2-bromonaphthalene with 3-ethylenedioxybutene (II) in the presence of a bivalent palladium salt and a phosphine, the reaction takes place extremely rapidly without operating under pressure and the 6-methoxy-2-(3-ethylenedioxybuten-1-yl)naphthalene (III) is obtained in optimum yields.

It has also been found that this product can be subjected, in two in situ operations, to hydrogenation and hydrolysis in order to obtain pure nabumetone in a practically quantitative yield.

The present invention therefore relates to a process for the preparation of nabumetone, characterised in that:

(a) 6-methoxy-2-bromonaphthalene is treated with 3-ethylenedioxybutene in the presence of a bivalent palladium salt and a phosphine;

(b) the 6-methoxy-2-(3-ethylenedioxybuten-1-yl) naphthalene so obtained (be) is subjected to catalytic hydrogenation and then (b₂) to acid hydrolysis, the process being illustrated by the following scheme:

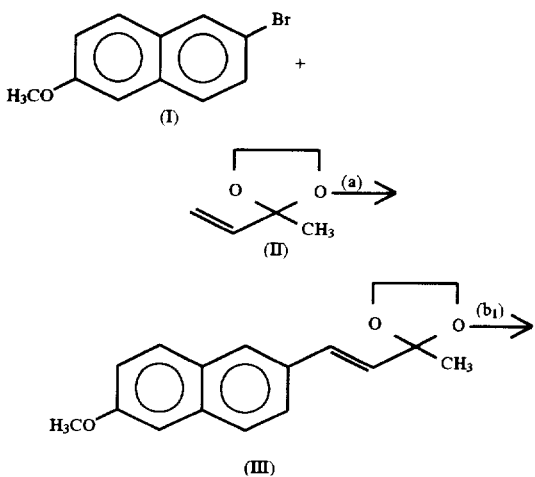

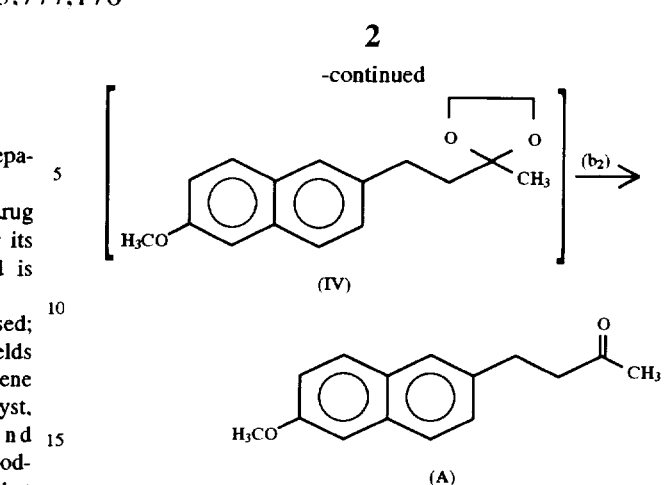

Stage (a) is carried out in a polar aprotic solvent, such as N,N-dimethylformamide or N,N-dimethylacetamide, preferably at a temperature of from 140° to 150° C.

A bivalent palladium salt, such as $PdCl_2$ or $Pd(OCOCH_3)_2$, may be used as the catalyst, and a phosphine, such as triphenylphosphine, is preferably used as the co-catalyst.

The molar ratio of the 6-methoxy-2-bromo-naphthalene to the catalyst, the bivalent palladium salt, is from 0.05% to 0.4%, preferably from 0.1% and 0.2% in moles, based on the moles of 6-methoxy-2-bromonaphthalene. The molar ratio of 6-methoxy-2-bromonaphthalene to the co-catalyst, the phosphine, is from 0.1% to 0.8%, preferably from 0.2% to 0.4% in moles, based on the moles of 6-methoxy-2-bromonaphthalene.

The reaction, carried out in the presence of an alkali carbonate or bicarbonate, is complete after from 15 to 60 minutes and the 6-methoxy-2-(3-ethylenedioxybuten-1-yl) naphthalene is isolated by concentrating the reaction mixture, taking up the residue in a hydrocarbon solvent, for example toluene, and, after optional heating, eliminating the solid secondary products and evaporating the solvent.

Stage (b₁) is carried out by catalytic hydrogenation, preferably using the same solvent as in stage (a), although the choice of solvent is not critical.

A metal such as palladium, platinum or nickel, on a suitable support, is used as the hydrogenation catalyst. Raney nickel is the preferred catalyst.

At the end of the hydrogenation operation, after the elimination of the catalyst, in stage (b₂), the solution contains the intermediate V which is preferably not isolated but subjected directly to acid hydrolysis, and therefore it is treated with water and an acid, preferably hydrochloric acid, at a temperature of from 20° to 80° C. In general, after from 45 to 75 minutes at from 55° to 75° C., the hydrolysis reaction is complete and the nabumetone is isolated by adding water to the mixture and leaving the nabumetone to crystallise.

The nabumetone so obtained, in yields which may reach 90% of the theoretical yield based on initial 6-methoxy-2-bromonaphthalene, is sufficiently pure but can be further purified by crystallisation from a $(C_1-C_3)$alkanol.

6-methoxy-2-(3-ethylenedioxybuten-1-yl)-naphthalene is a new compound to which the present invention also relates.

The following Example illustrates the invention without, however, limiting it.

EXAMPLE (a) A mixture of 25 g of 6-methoxy-2-bromo-naphthalene (I), 0.025 g of $PdCl_2$, 0.075 g of triphenylphosphine, 15 g of 3-ethylenedioxybutene (II) and 10 g of anhydrous sodium carbonate in 250 ml of N,N-dimethylacetamide is heated to 145° C. After 8 hours at that temperature, the reaction mixture is concentrated under a vacuum at 65° C. and the residue is taken up in 100 ml of toluene. After being decoloured with carbon, the solution is heated at 60° C for one hour and then it is cooled to ambient temperature and filtered. The clear solution so obtained is concentrated under a vacuum at from 40° to 50° C. and the residue is taken up in cyclohexane from which the 6-methoxy-2-(3-ethylenedioxybuten-1-yl) naphthalene (III) crystallises. 27.8 g of dry product are thus obtained (yield: 98%).

$^1$H-NMR (200 MHz, CDCl$_3$, ppm): 1.60 (3H, s, CH$_3$); 3.92 (3H, s, OCH$_3$); 3.97–4.90 (4H, m, CH$_2$CH$_2$); 6.22 (1H, d, J=16.1 Hz); 6.84 (1H, d, J=16.1 Hz); 7.11–7.26 (2H, m, arom.); 7.54–7.73 (4H, m, arom.).

(b) A mixture of 8 g of the product so obtained and 3 g of Raney nickel in 40 ml of N,N-dimethylacetamide is hydrogenated for 6 hours at from 35 to 40° C. and 49.3x10$^6$ Pa and then decanted. The liquid containing the 6-methoxy-2-(3-ethylenedioxybuten-1-yl) naphthalene (IV) is separated and the temperature is increased to 60° C. and 60 ml of distilled water and 2 ml of concentrated hydrochloric acid are added. After one hour at 60° C., a further 60 ml of water are added and the whole is left to recrystallise. 6.49 g of nabumetone (A) are obtained with a purity in conformity with the USP standard (yield: 96%).

I claim:

1. Process for the preparation of nabumetone, characterised in that:

(a) 6-methoxy-2-bromonaphthalene is treated with 3-ethylenedioxybutene in the presence of a bivalent palladium salt as a catalyst and a phosphine as a co-catalyst (b) the 6-methoxy-2-(3-ethylenedioxybuten-1-yl) naphthalene so obtained (b$_1$) is subjected to catalytic hydrogenation and then (b$_2$) to acid hydrolysis.

2. Process according to claim 1, characterised in that the bivalent palladium salt is present in amounts of from 0.05% to 0.4% in moles based on the moles of 6-methoxy-2-bromonaphthalene.

3. Process according to claim 2, characterised in that the bivalent palladium salt is present in amounts of from 0.1% to 0.2% in moles based on the moles of 6-methoxy-2-bromonaphthalene.

4. Process according to claim 1, characterised in that the phosphine is present in amounts of from 0.1% to 0.8% in moles based on the moles of 6-methoxy-2-bromonaphthalene.

5. Process according to claim 4, characterised in that the phosphine is present in amounts of from 0.2% to 0.4% in moles based on the moles of 6-methoxy-2-bromonaphthalene.

6. Process according to claim 1, characterised in that the phosphine is triphenylphosphine.

7. Process according to claim 1, characterised in that stage (a) is carried out using PdCl$_2$ and triphenylphosphine, at a temperature of from 140° to 150° C. in a polar aprotic solvent.

8. Process according to claim 7, characterised in that N,N-dimethylacetamide is used as the solvent.

9. Process according to claim 1, characterised in that stage (b) is effected by hydrogenation in the presence of Raney nickel and by subsequent hydrolysis with aqueous hydrochloric acid.

10. 6-Methoxy-2-(3-ethylenedioxybuten-1-yl)-naphthalene.

* * * * *